(12) United States Patent
McKenna et al.

(10) Patent No.: US 7,645,288 B2
(45) Date of Patent: Jan. 12, 2010

(54) ANASTOMOTIC RING APPLIER WITH INFLATABLE MEMBERS

(75) Inventors: Robert H. McKenna, Cincinnati, OH (US); Mark S. Ortiz, Milford, OH (US); David B. Griffith, Cincinnati, OH (US); Robert J. Simms, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 491 days.

(21) Appl. No.: 11/122,761

(22) Filed: May 5, 2005

(65) Prior Publication Data

US 2006/0253039 A1    Nov. 9, 2006

(51) Int. Cl.
*A61B 17/08* (2006.01)
*A61B 17/10* (2006.01)

(52) U.S. Cl. ..................... 606/153

(58) Field of Classification Search ......... 606/139–141, 606/151, 153, 157, 198; 604/96.01, 97.01, 604/99.01, 99.04, 101.01, 101.03, 101.05, 604/103.03, 103.05, 103.08, 104–113; 600/214, 600/216
See application file for complete search history.

(56) References Cited

U.S. PATENT DOCUMENTS

| | | | |
|---|---|---|---|
| 4,611,602 A | 9/1986 | Bolduc | |
| 4,943,280 A | 7/1990 | Lander | |
| 4,971,034 A | 11/1990 | Doi et al. | |
| 5,053,016 A | 10/1991 | Lander | |
| 5,127,909 A | 7/1992 | Shichman | |
| 5,226,876 A | 7/1993 | Filipi et al. | |
| 5,345,949 A * | 9/1994 | Shlain ................. | 128/898 |
| 5,425,738 A * | 6/1995 | Gustafson et al. ...... | 606/153 |
| 5,855,312 A | 1/1999 | Toledano | |
| 6,171,321 B1 | 1/2001 | Gifford et al. | |
| 6,451,029 B1 * | 9/2002 | Yeatman .............. | 606/139 |
| 6,485,496 B1 * | 11/2002 | Suyker et al. .......... | 606/153 |

(Continued)

FOREIGN PATENT DOCUMENTS

EP        1340462        9/2003

(Continued)

OTHER PUBLICATIONS

Office Action dated Jan. 4, 2006, for U.S. Appl. No. 10/675,497, filed Sep. 30, 2003.

(Continued)

*Primary Examiner*—Tan Uyen (Jackie) T Ho
*Assistant Examiner*—Dianne Dornbusch

(57) ABSTRACT

A surgical instrument comprises a handle connected to a shaft and a pair of inflatable members. The shaft includes conduits for communicating a pressurized medium to the inflatable members and an insufflation tube. The handle includes a port for communicating a pressurized medium to the conduits and a port for communicating a pressurized medium to the insufflation tube. After an anastomotic ring has been deployed, the shaft may be positioned such that an inflatable member is positioned within each of the lumens joined by the anastomosis, such that an inflatable member is located on each side of the anastomosis. The inflatable members may be inflated to provide a seal in each of the lumens. With each of the lumens sealed by the inflatable members, the anastomosis site may be insufflated through the insufflation tube to leak or pressure test the anastomosis.

11 Claims, 21 Drawing Sheets

U.S. PATENT DOCUMENTS

| | | | |
|---|---|---|---|
| 6,645,240 B2 * | 11/2003 | Yee | 623/1.11 |
| 2002/0183769 A1 | 12/2002 | Swanson | |
| 2003/0032967 A1 | 2/2003 | Park et al. | |
| 2003/0229364 A1 * | 12/2003 | Seiba | 606/153 |
| 2005/0059992 A1 | 3/2005 | Leiboff | |
| 2006/0217637 A1 | 9/2006 | Leiboff et al. | |

FOREIGN PATENT DOCUMENTS

EP        1520531        4/2005

OTHER PUBLICATIONS

European Search Report, dated Sep. 29, 2006, for EP Application No. 06252383.2.

* cited by examiner

ANASTOMOTIC RING APPLIER WITH INFLATABLE MEMBERS

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

Upon deployment of an anastomotic ring at an anastomosis site, it may be desirable to test the anastomosis for leaking or other integrity issues. Such testing may involve sealing both lumens being affected by the anastomosis, and insufflating the anastomosis site. It may also be desirable to effect such testing with the same device that was used to deploy the anastomotic ring.

BRIEF SUMMARY OF THE INVENTION

Embodiments of the invention provide an anastomotic ring applier device that is capable of leak and/or pressure testing an anastomosis, thereby allowing a surgeon to confirm the integrity of the anastomosis.

In one embodiment, a surgical instrument comprises a handle and a shaft connected to the handle. The shaft comprises an outer surface, a proximal end, a distal end, and one or more conduits. The handle is located at the proximal end of the shaft. The distal end of the shaft comprises two or more inflatable members adjacent the outer surface. The two or more inflatable members are spaced to permit at least one of the inflatable members to be positioned on a first side of an anastomosis and another at least one inflatable member to be positioned on a second side of the anastomosis. The one or more conduits are configured to communicate a pressurized medium to at least one of the two or more inflatable members.

In another embodiment, a surgical instrument comprises an elongate shaft, a ring deployment mechanism in communication with the shaft, and at least one inflatable member in communication with the shaft. The ring deployment mechanism is operable to deploy an anastomotic ring device at an anastomosis site. The at least one inflatable member is configured to provide a seal of at least one lumen of an anastomosis site. The seal is adjacent the anastomosis, and is provide upon inflation of the at least one inflatable member.

In yet another embodiment, a method for testing an anastomosis comprises providing an instrument at the anastomosis site. The instrument comprises an elongate shaft, two inflatable members in communication with the shaft, one or more conduits configured to communicate a pressurized fluid to the inflatable members, and an insufflation member. The two inflatable members are spaced to permit one of the inflatable members to be positioned in one of the lumens of the anastomosis site and the other of the inflatable members to be positioned in the other lumen of the anastomosis site. The insufflation member is configured to communicate a pressurized fluid to the anastomosis site. The method further comprises inflating the inflatable members. The act of inflating the inflatable members comprises communicating a pressurized fluid to the inflatable members via the one or more conduits. Upon inflation of the inflatable members, each lumen of the anastomosis site is sealed. The method further comprises insufflating the anastomosis site. The act of insufflating the anastomosis site comprises communicating a pressurized fluid to the anastomosis site via the insufflation member. The act of insufflating is performed upon the lumens of the anastomosis site being sealed by the inflatable members. The method further comprises releasing pressurized fluid from the inflatable members and removing the instrument from the patient.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

DETAILED DESCRIPTION OF EMBODIMENTS OF THE INVENTION

Figure 1:
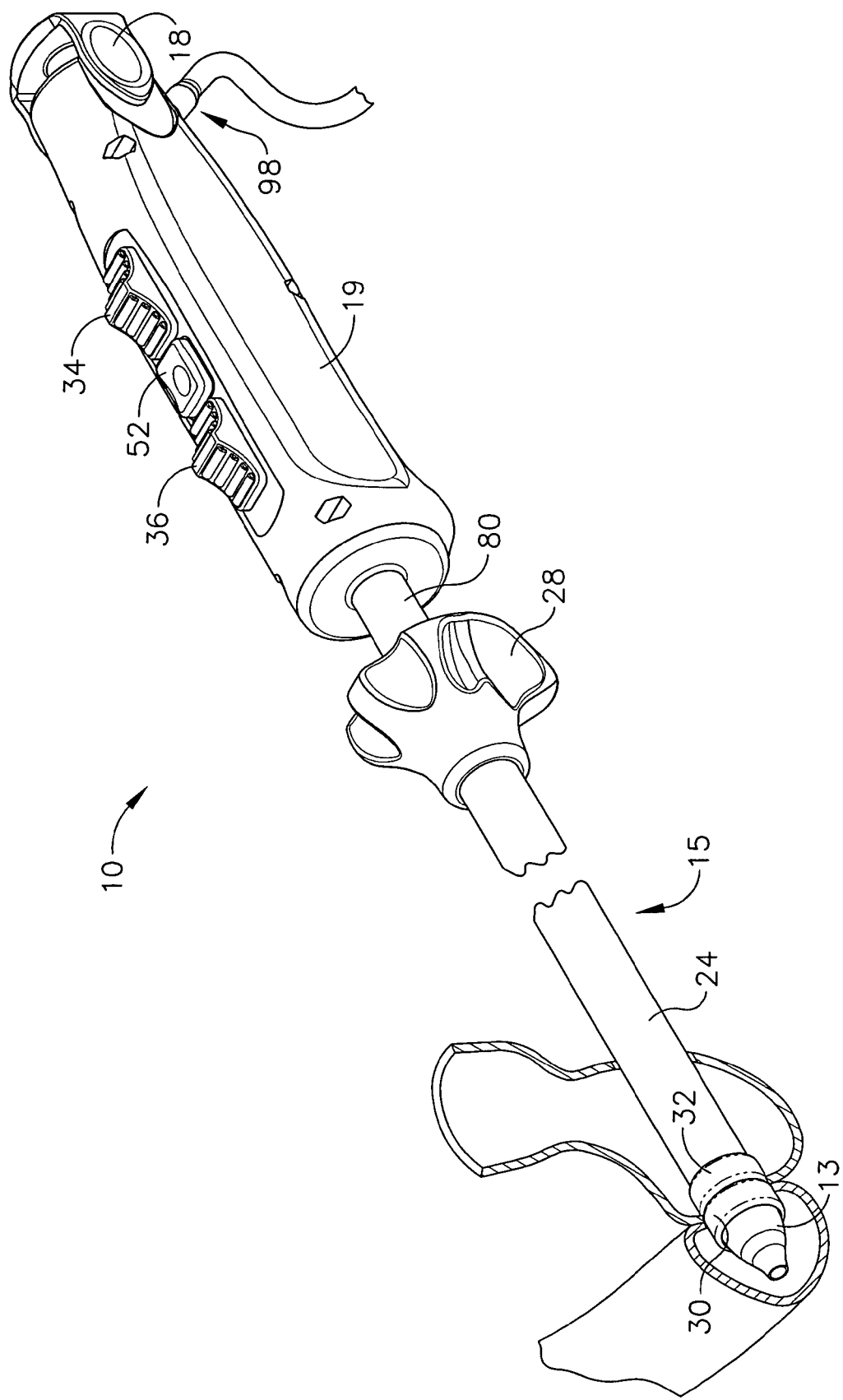
FIG. 1 is a perspective view of an anastomotic ring applier device, shown with a retracted tip.
Figure 2:
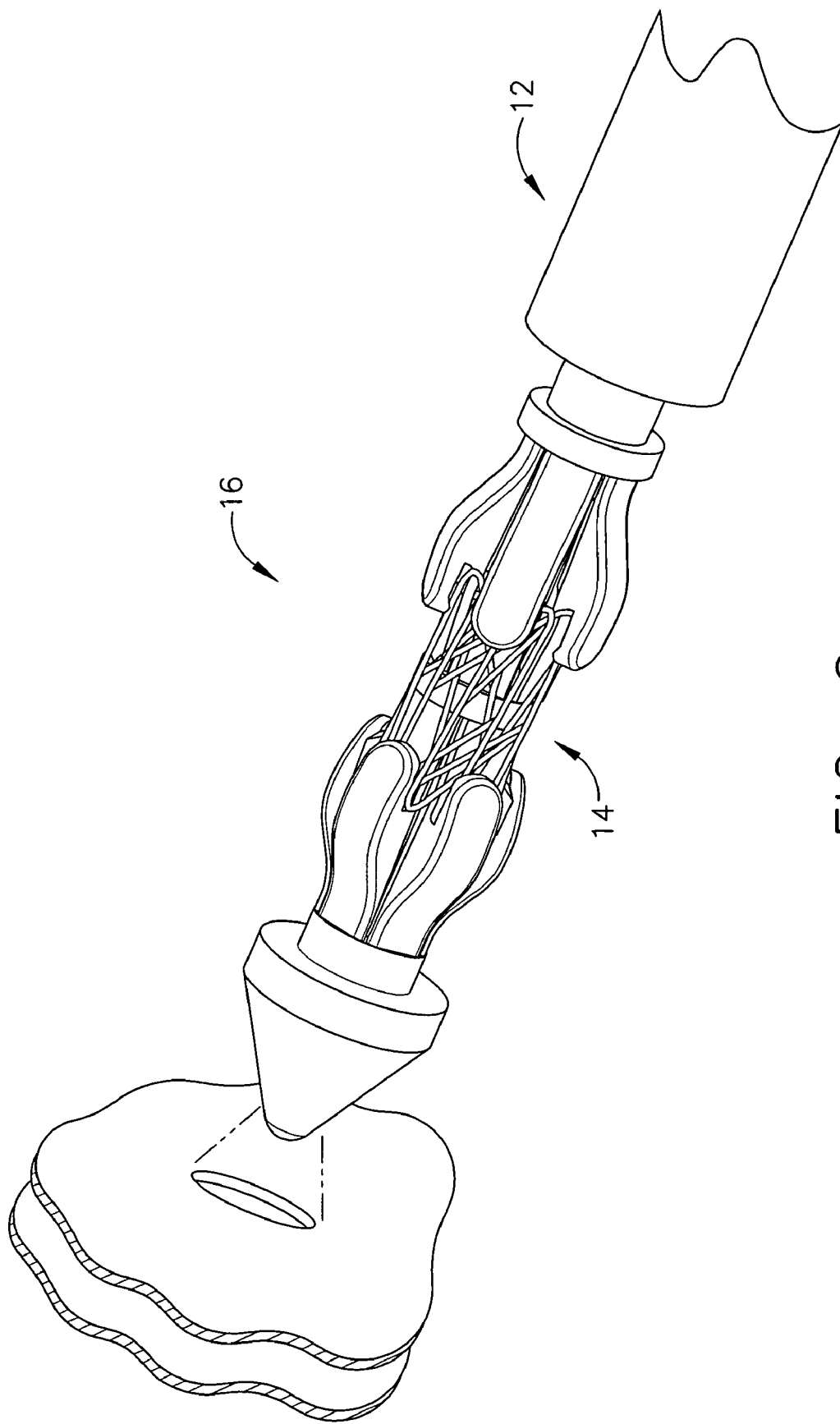
FIG. 2 is a partial perspective view of the distal portion of an anastomotic ring applier device holding an anastomotic ring in an unactuated position.
Figure 3:
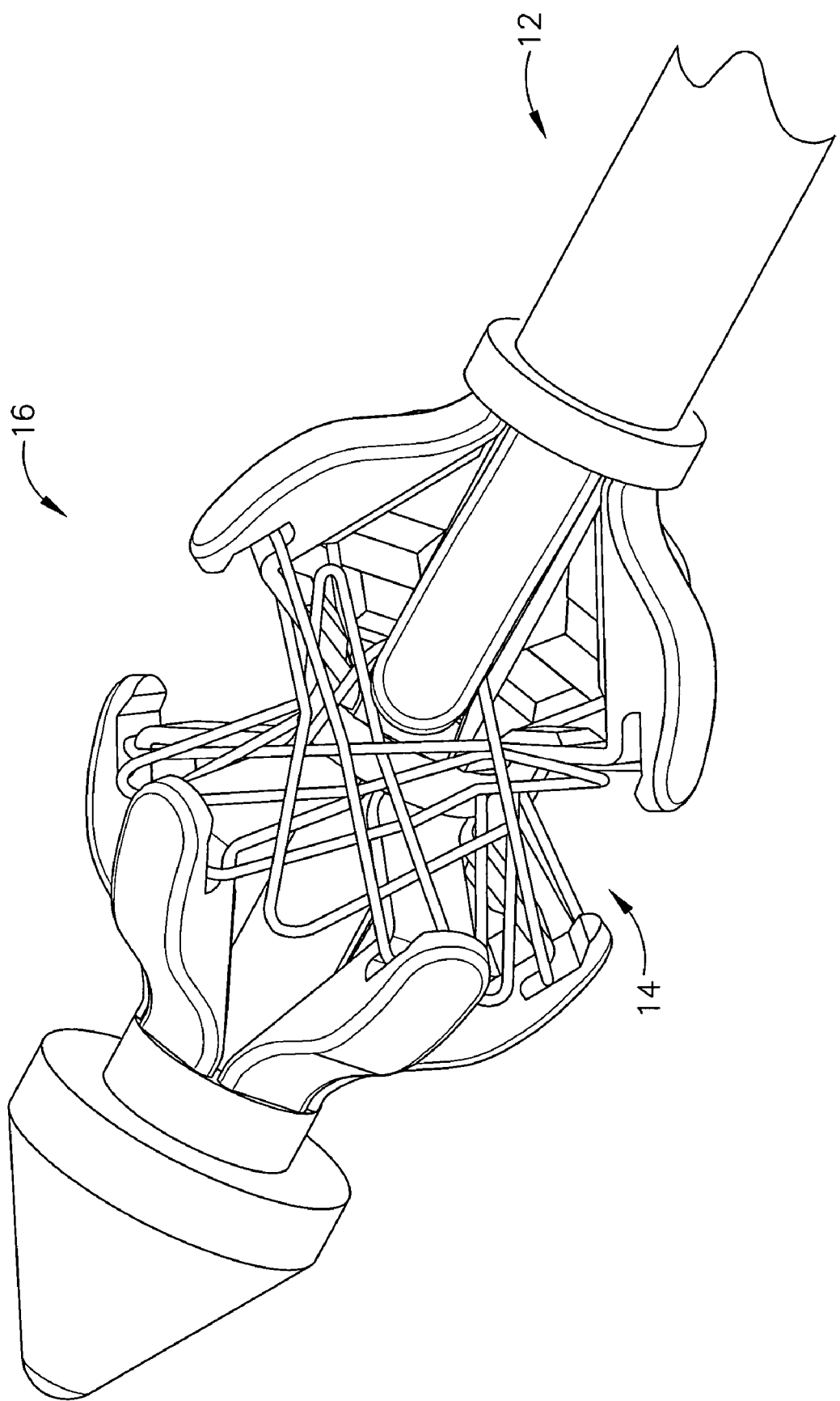
FIG. 3 is a partial perspective view of the distal portion of the device of FIG. 2 holding an anastomotic ring in the actuated position.
Figure 4:
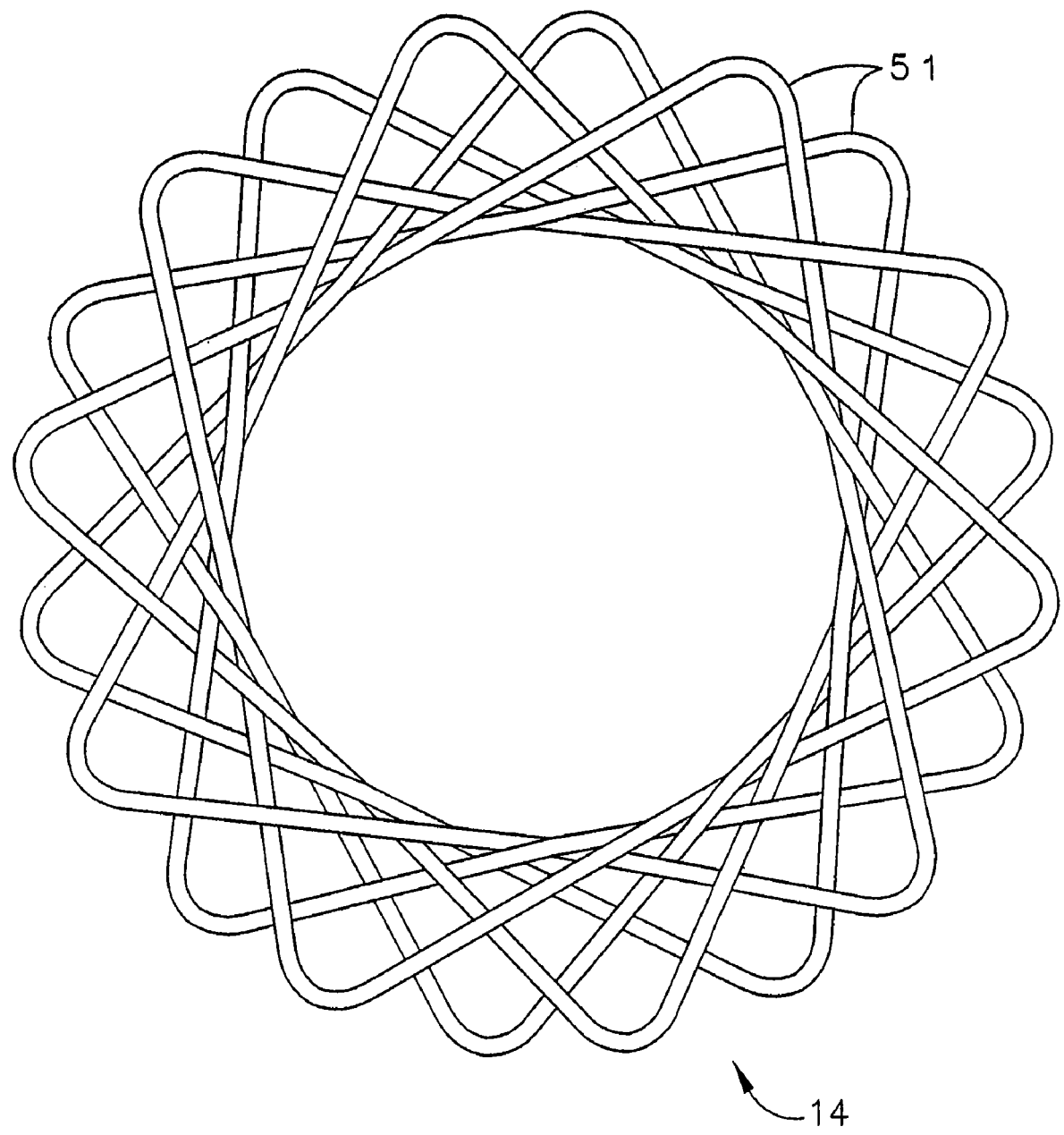
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Referring to FIGS. 1 and 5-9, applier 10 of the present example is operable to deploy an anastomotic ring. As shown, applier 10 of the present example comprises a tip 13, a shaft 15, and a handle 19. Shaft 15 comprises a tubular sheath 24. Tubular sheath 24 is moveable from a first position to a second position. Shaft 15 further comprises a ring deployment mechanism 26 located at its distal end, proximal of tip 13. In the first position, sheath 24 is configured to cover ring deployment mechanism 26 (FIGS. 1 and 13) to prevent tissue from catching on deployment mechanism 26 during insertion and extraction of applier 10. Sheath 24 is configured such that deployment mechanism 26 is exposed and free to actuate when sheath 24 is in the second position (FIGS. 6-10 and 15-19). Applier 10 further comprises a sheath actuator 28 operable to move sheath 24 between the first and second positions. Suitable alternatives to sheath 24 and/or sheath actuator 28 will be apparent to those of ordinary skill in the art. Applier 10 of the present example also includes a tip actuator 18 located on handle 19. Tip actuator 18 is operable to move tip 13 from a retracted position (shown in FIGS. 1 and 13) to an extended position (shown in FIGS. 5-10 and 14-19). Such movement is effected through communication of motion by tip tube 90, which is fixedly secured to tip 13 and tip actuator 18. Tip tube 90 is located within shaft 15, and is coaxially aligned with sheath 24.

A distal balloon 30 is circumferentially disposed about a proximal portion of tip 13. A proximal balloon 32 is circumferentially disposed about a distal portion of sheath 24. Uses for and other features of distal and proximal balloons 30, 32 will be discussed in detail below.

Figure 6:
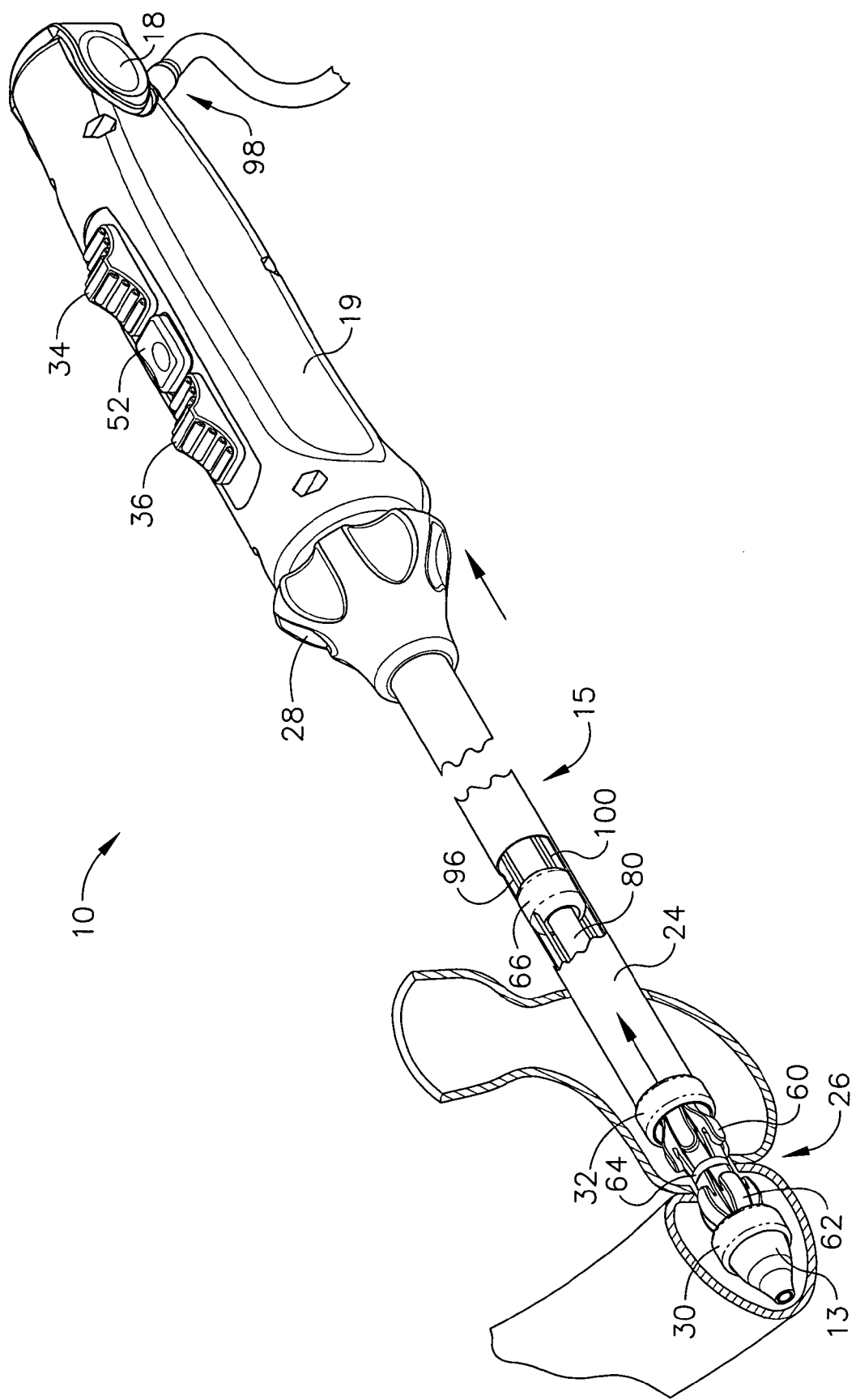
FIG. 6 is a perspective view of the device of FIG. 1, shown with the sheath retracted.
Figure 7:
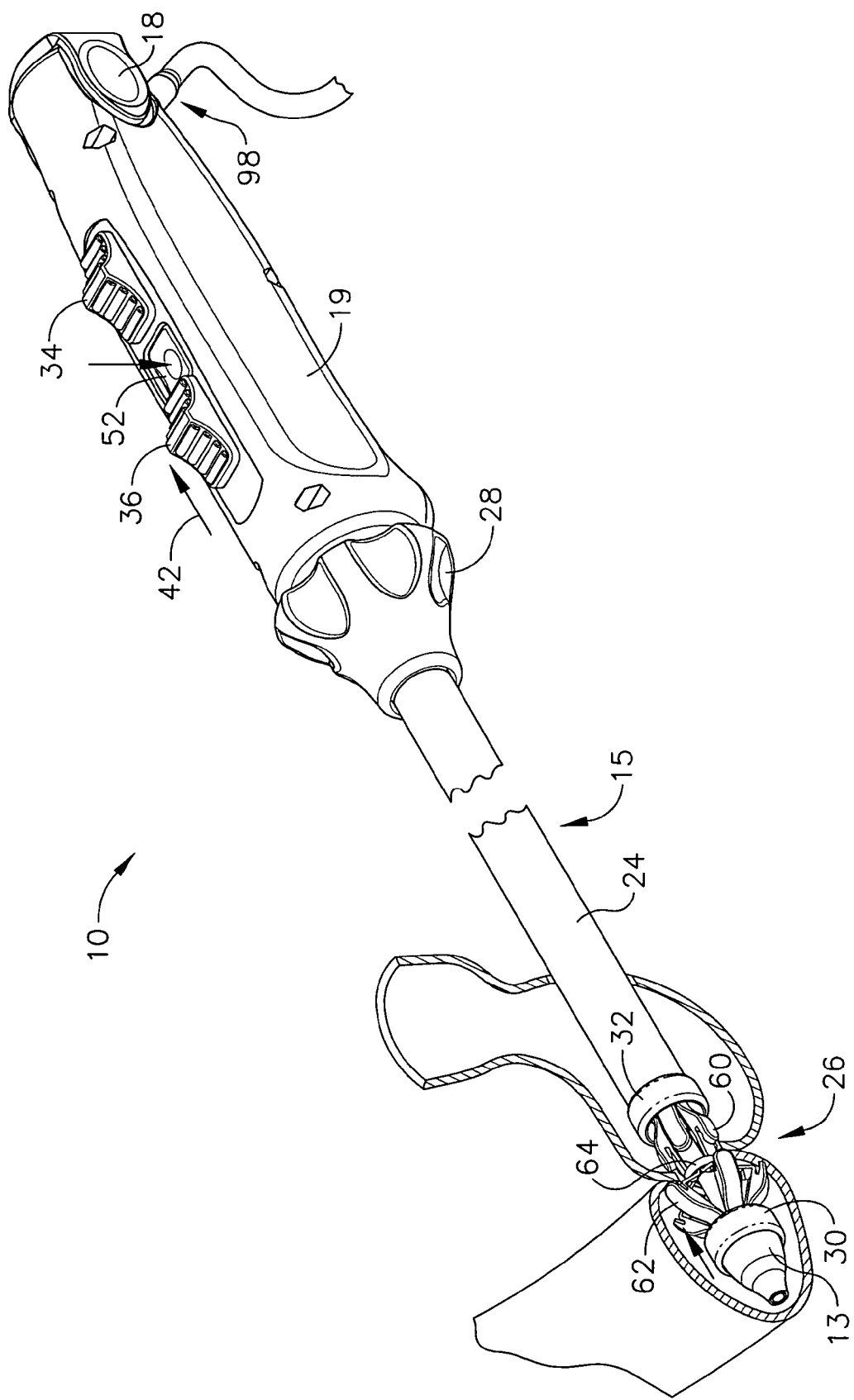
FIG. 7 is a perspective view of the device of FIG. 1, shown with a distal portion of the ring deployment mechanism actuated.
Figure 8:
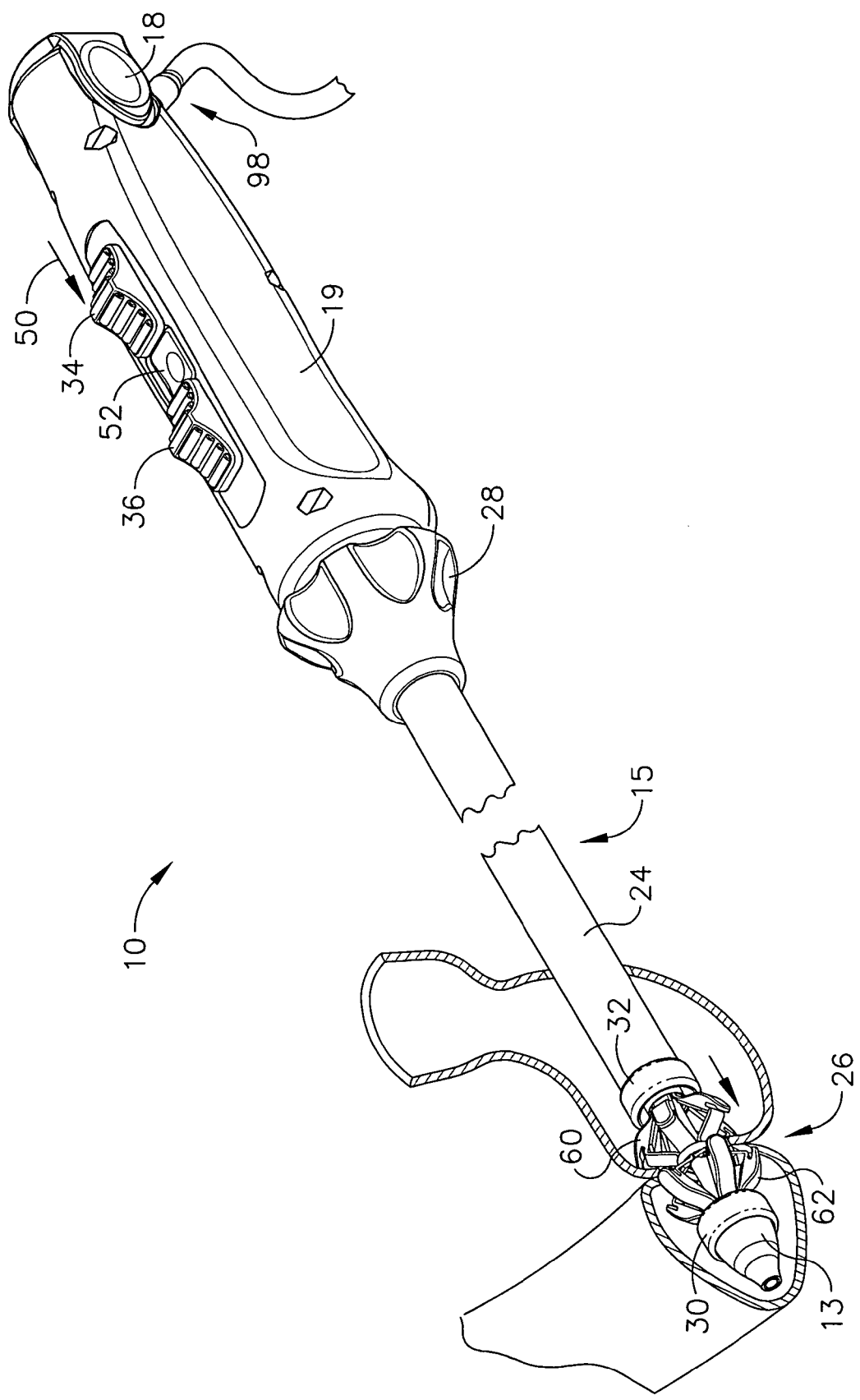
FIG. 8 is a perspective view of the device of FIG. 1, shown with both a distal portion and a proximal portion of the ring deployment mechanism partially actuated.
Figure 13:
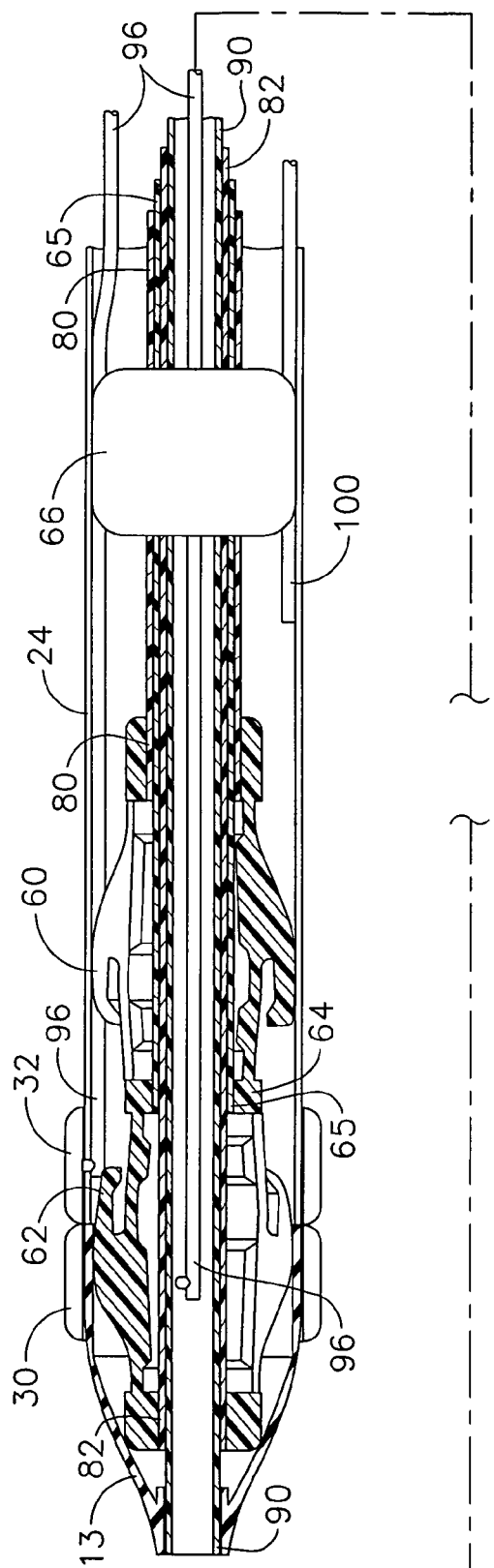
FIG. 13 is a partial cross-sectional view of distal and proximal portions of the device of FIG. 1, shown with a retracted tip.
Figure 13:
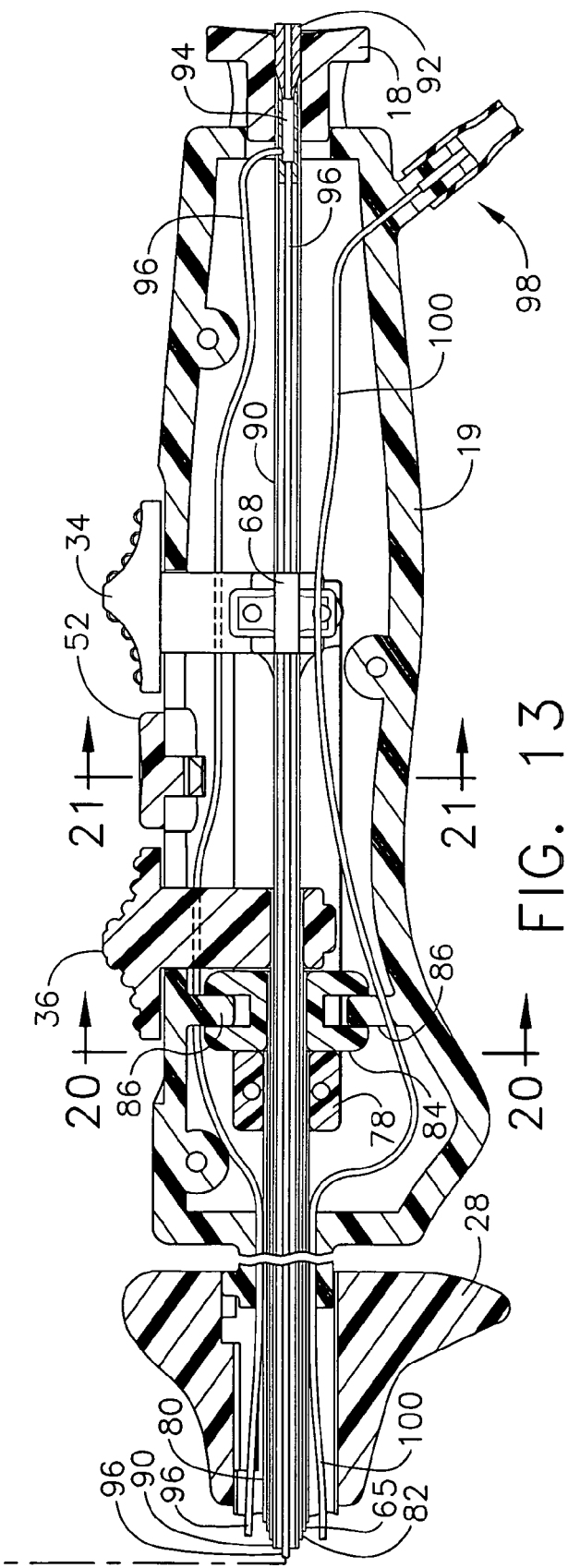
Figure 14:
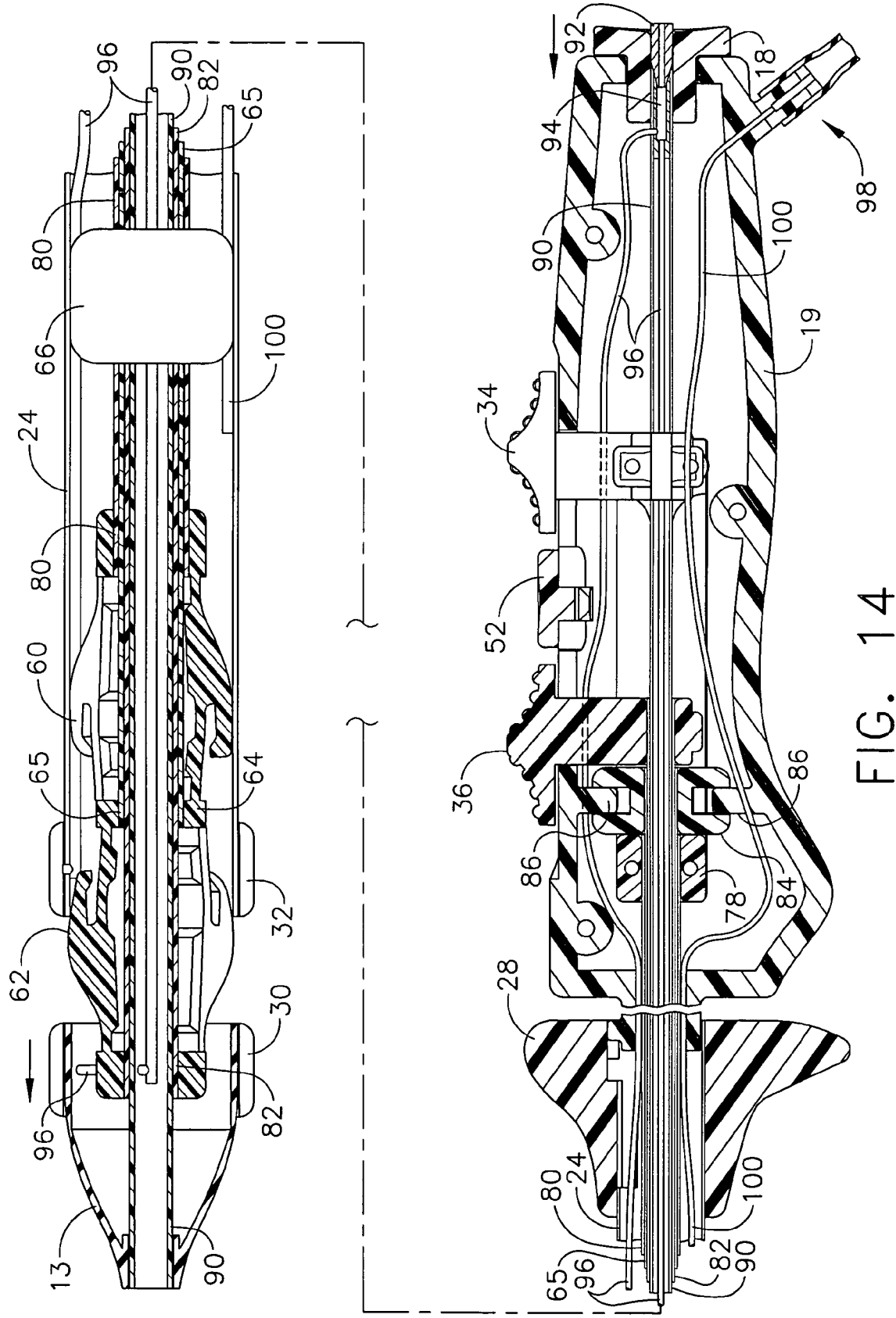
FIG. 14 is a partial cross-sectional view of distal and proximal portions of the device of FIG. 1, shown with the tip extended.

Referring now to FIGS. 6-11 and 13-19, ring deployment mechanism 26 of the present example comprises a set of proximal fingers 60 and a set of distal fingers 62. Handle 19 of applier 10 further comprises a pair of deployment actuators 34, 36. As described in more detail below, first deployment actuator 34 is operable to actuate proximal fingers 60 of ring deployment mechanism 26; and second deployment actuator 36 is operable to actuate distal fingers 62 of ring deployment mechanism 26. In FIGS. 7 and 13, distal fingers 62 are shown in the actuated position for deploying a distal portion of an anastomotic ring 14. Arrow 42 depicts actuating motion of second actuator 36. In FIGS. 8 and 14, proximal fingers 60 are shown in the actuated position for deploying a proximal portion of anastomotic ring 14 to complete an anastomotic attachment between proximate tissue walls. Arrow 50 depicts the actuating motion of first actuator 34.

Both proximal fingers 60 and distal fingers 62 are in a double-hinged relationship with a stationary mid-ring 64 of ring deployment mechanism 26. Proximal fingers 60 are configured to slide toward mid-ring 64 in response to actuation of first actuator 34, which causes proximal fingers 60 to actuate outwardly relative to shaft 15. Mid-ring 64 is held stationary by a stationary ground tube 65. Similarly, distal fingers 62 are configured to slide toward mid-ring 64 in response to actuation of second actuator 36, which causes distal fingers 62 to actuate outwardly relative to shaft 15. Fingers 60, 62 are configured to hold an anastomotic ring 14 by engaging petals 51 prior to and during deployment of the anastomotic ring 14, and release petals 51 upon deployment of the anastomotic ring 14.

As shown in FIGS. 11 and 13-20, the above-described actuating components of ring deployment mechanism 26 comprise a series of concentric tubes 82, 65, 80, which are located within shaft 15. As will be discussed in greater detail below, an inner tube 82 is configured to transmit actuating force to distal fingers 62, while an outer tuber 80 is configured to transmit actuating force to proximal fingers 60. While, in the present example, tip tube 90 is not configured to transmit actuating force to ring deployment mechanism 26, tip tube 90 is coaxially aligned with concentric tubes 82, 65, 80, and is located within inner tube 82. A bushing 66 is included within shaft 15 to keep the concentric tubes 82, 65, 80 and tip tube 90 centered. It will be appreciated, however, that the above-described components need not be concentrically or coaxially aligned, and that any suitable alternative to bushing 66 may be used. Similarly, any suitable alternative to tubes 82, 65, 80, 90 may be used, including but not limited to cables and the like.

It will also be appreciated that any suitable alternative(s) to ring deployment mechanism 26 and/or deployment actuators 34, 36 may be used.

To prevent inadvertent deployment of ring deployment mechanism 26, applier 10 of the present example is provided with a locking element 52. In the present example, locking element 52 is operable to move from a locked position to an unlocked position. In FIGS. 1, 5-6, 10, 13-15, and 19, locking element 52 is shown in a locked position preventing actuating movement of first actuator 34 and second actuator 36. In FIGS. 7-9 and 17-18, locking element 52 is shown in the unlocked position, allowing actuators 34, 36 to move to the actuated position.

As stated above, first deployment actuator 34 of the present example is operable to control proximal fingers 60 and second deployment actuator 36 is operable to control distal fingers 62. Referring now to FIGS. 12-21, first and second ring deployment actuators 34, 36 each have a pair of grooves 67 that are configured to slide on a track 68 of handle 19. As mentioned above, locking element 52 may be utilized to prevent inadvertent movement of first or second actuators 34, 36. In the present example, first actuator 34 is fixedly attached to a proximal portion 74 of track 68. Track 68 is slideable within handle 19. A distal portion 76 of track 68 is fixedly attached to a slider 78, which is fixedly secured to outer tube 80. Longitudinal motion of first actuator 34 is thereby operable to cause corresponding longitudinal motion of track 68, slider 78, and outer tube 80. Other suitable relationships between these components, as well as alternative components, will be apparent to those of ordinary skill in the art.

The proximal end of ground tube 65 is fixedly attached to anchor member 84. Anchor member 84 is configured to engage with bosses 86, which are integral with handle 19. Accordingly, in the present example, anchor member 84 and bosses 86 are configured to prevent relative movement between ground tube 65 and handle 19. Thus, ground tube 65 prevents relative longitudinal movement between mid-ring 64 of ring deployment mechanism 26 and handle 19. Of course, any other configuration may be used.

Second actuator 36 is connected to inner tube 82. Inner tube 82 extends longitudinally through ground tube 65. Inner tube 82 is operable to communicate motion to distal fingers 62. In this manner, first actuator 34 controls actuation of proximal fingers 60, and second actuator 36 controls actuation of distal fingers 62.

It should be noted that although second actuator 36 is configured to slide on track 68 in the present example, second actuator 36 is not statically attached to track 68. Therefore, longitudinal movement of track 68 caused by motion of first actuator 34 does not cause longitudinal movement of second actuator 36. Of course, handle 19 and components thereof may be configured in any other suitable way. By way of example only, first actuator 34 may be configured to control actuation of distal fingers 62, and second actuator 36 may be configured to control actuation of proximal fingers 60. Still other suitable alternative configurations will be apparent to those of ordinary skill in the art.

As shown, handle 19 further comprises a balloon port 92, which is located in tip actuator 18, Balloon port 92 is configured to receive a pressurized medium, such as air, liquid, or the like, from an external source. Balloon port 92 is in fluid communication with splitter 94, which is further in fluid communication with two balloon conduits 96. Each of the balloon conduits 96 is in fluid communication with a respective balloon 30, 32. Thus, a pressurized medium may be communicated to balloon port 92, and may be further communicated to each balloon 30, 32 via splitter 94 and balloon conduits 96. One of the balloon conduits 96 (the one that is in communication with distal balloon 30) is located inside tip tube 90, while the other balloon conduit 96 is located within sheath 24, outside of outer tube 80. Of course, any other positioning for balloon conduits 96 may be used.

Figure 10:
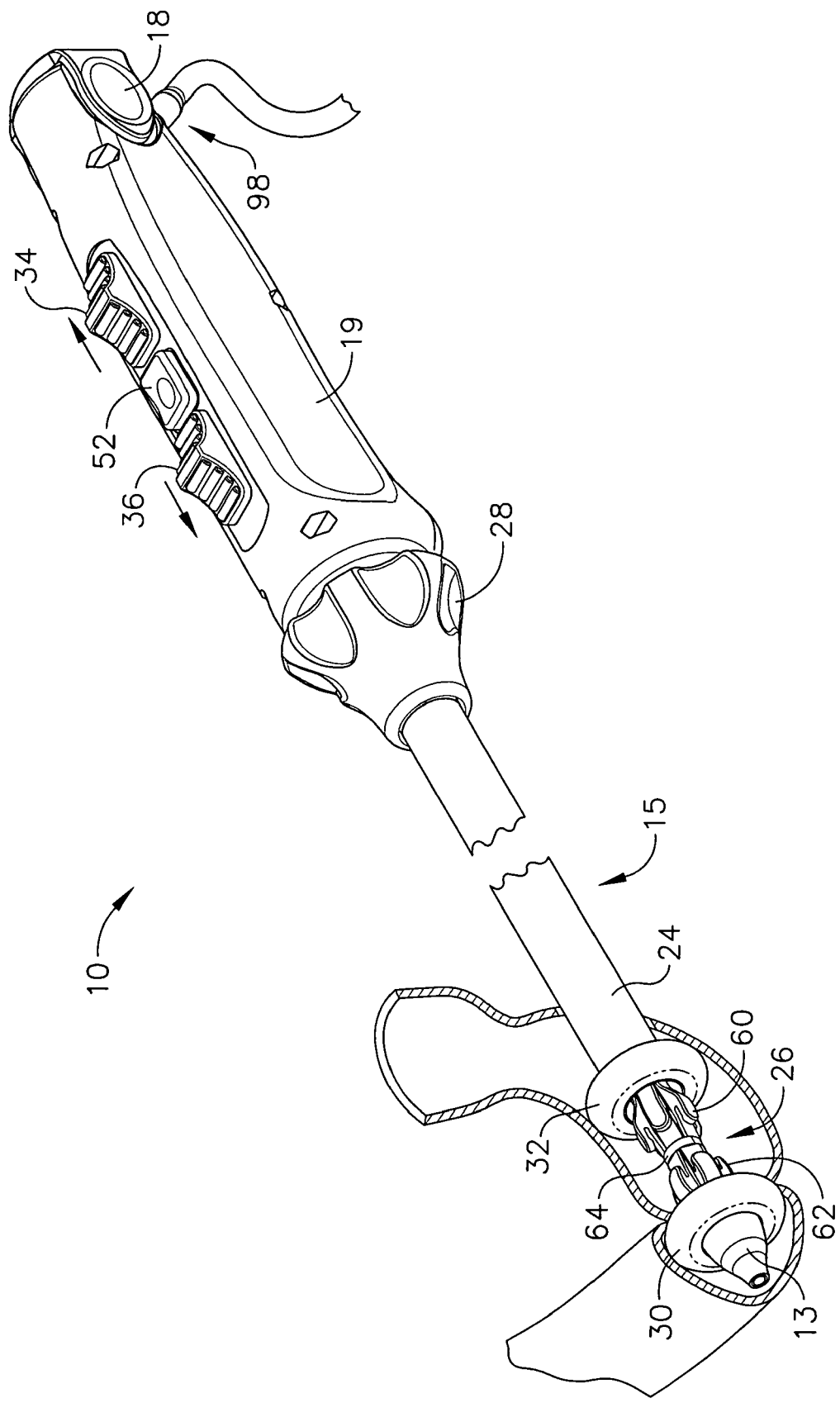
FIG. 10 is a perspective view of the device of FIG. 1, shown with balloons inflated.
Figure 11:
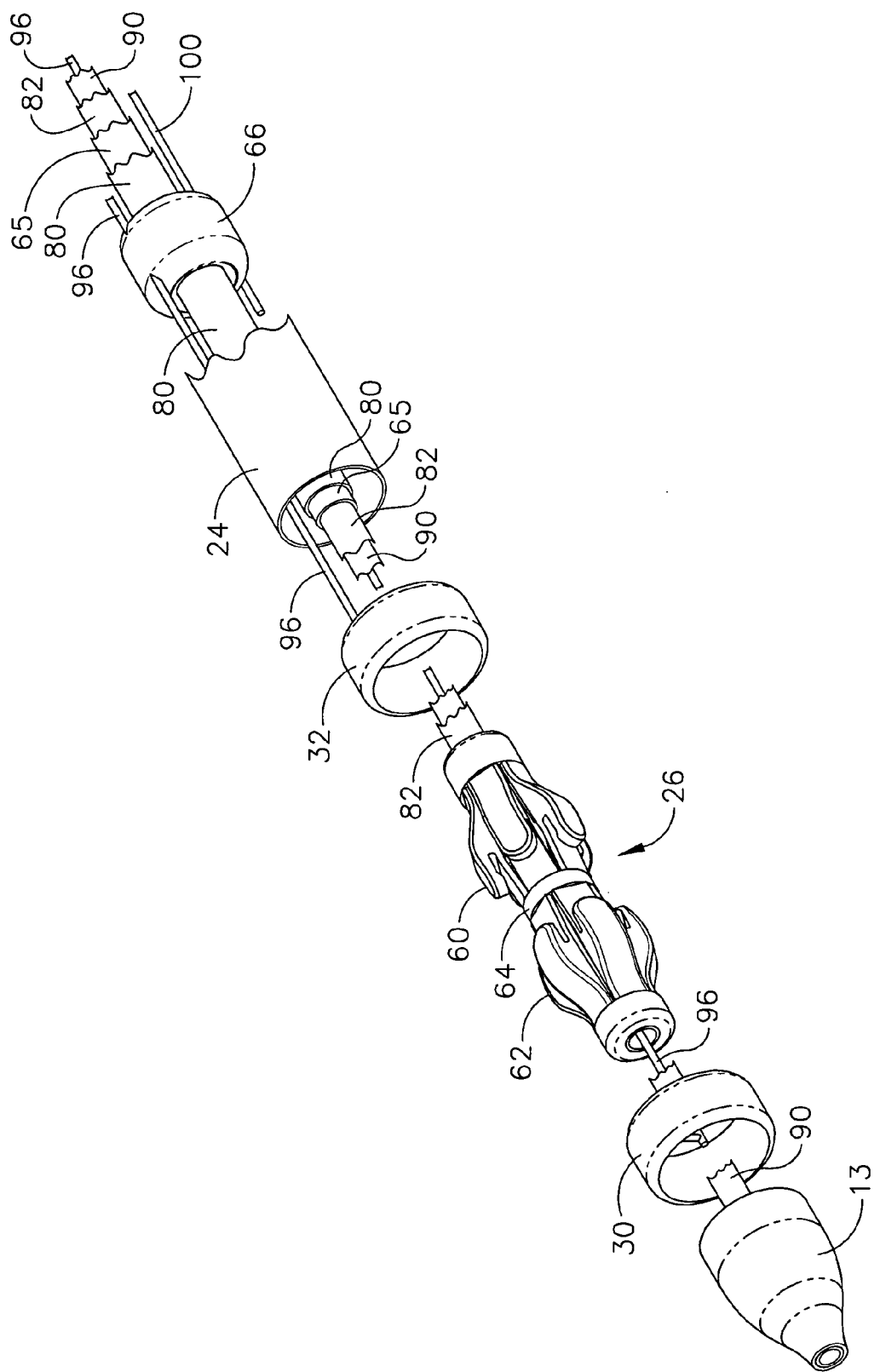
FIG. 11 is a partial exploded view of the distal portion of the device of FIG. 1.
Figure 12:
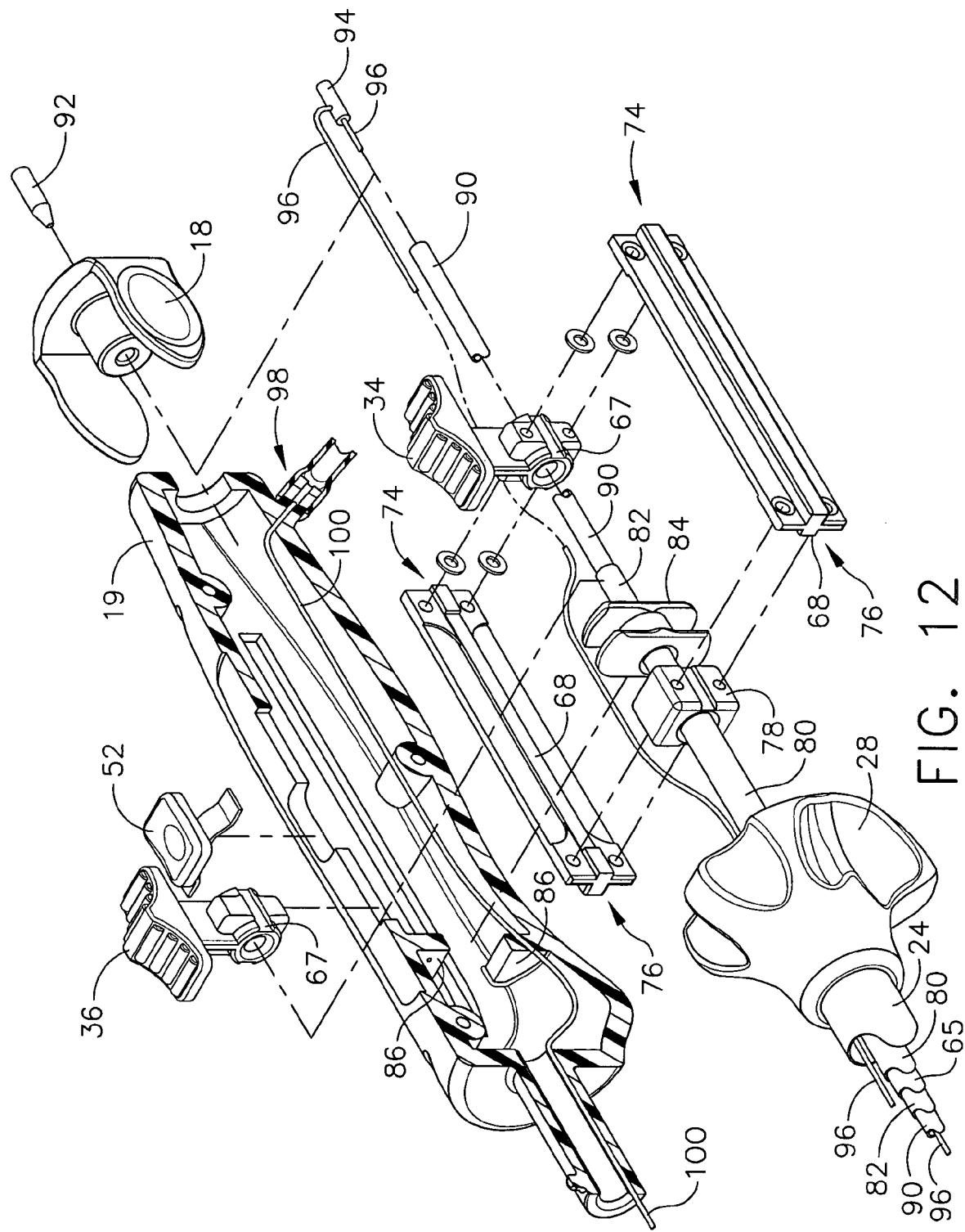
FIG. 12 is an exploded view of an actuation mechanism of the device of FIG. 1.
Figure 19:
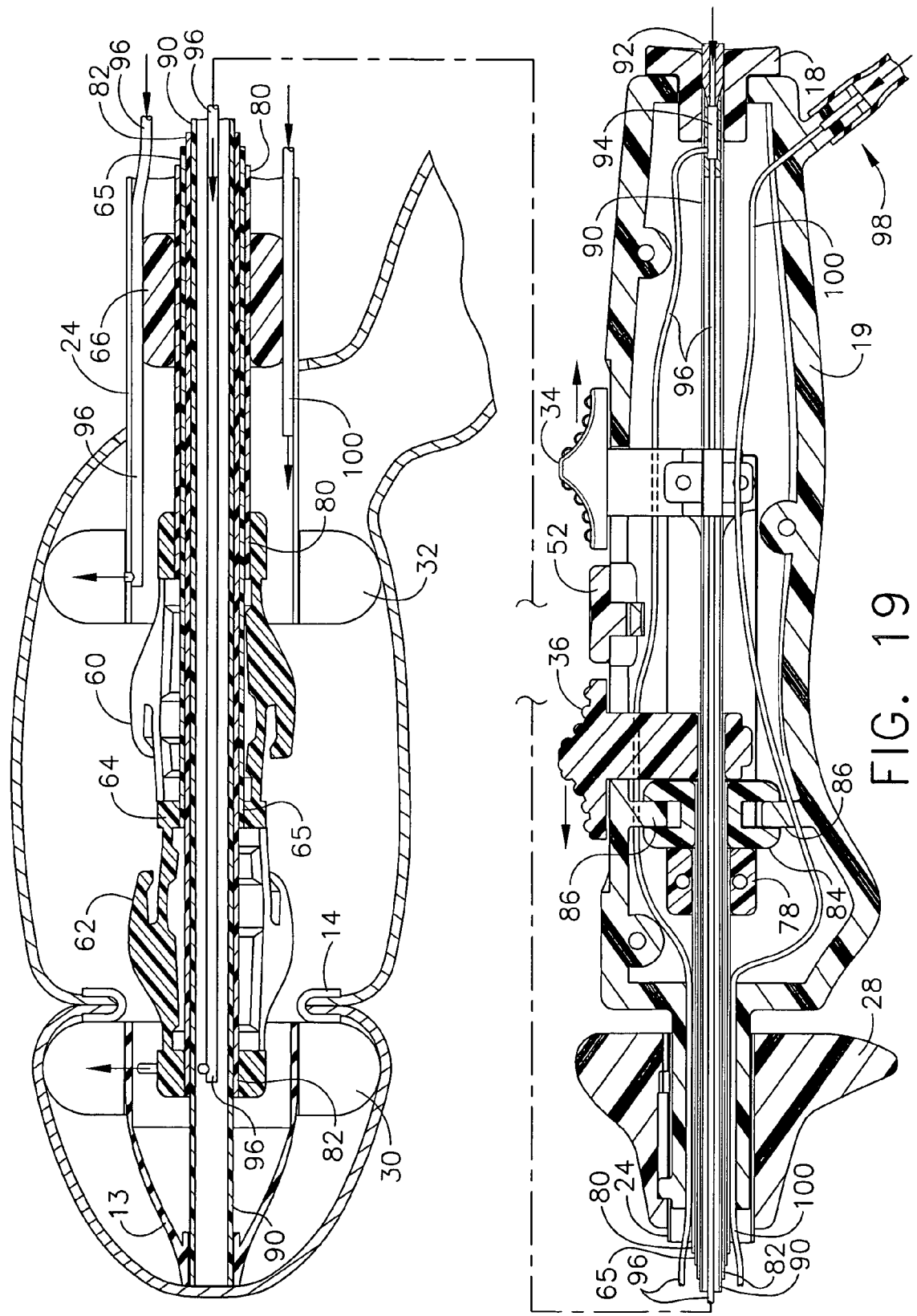
FIG. 19 is a partial cross-sectional view of distal and proximal portions of the device of FIG. 1, shown with balloons inflated.
Figure 20:
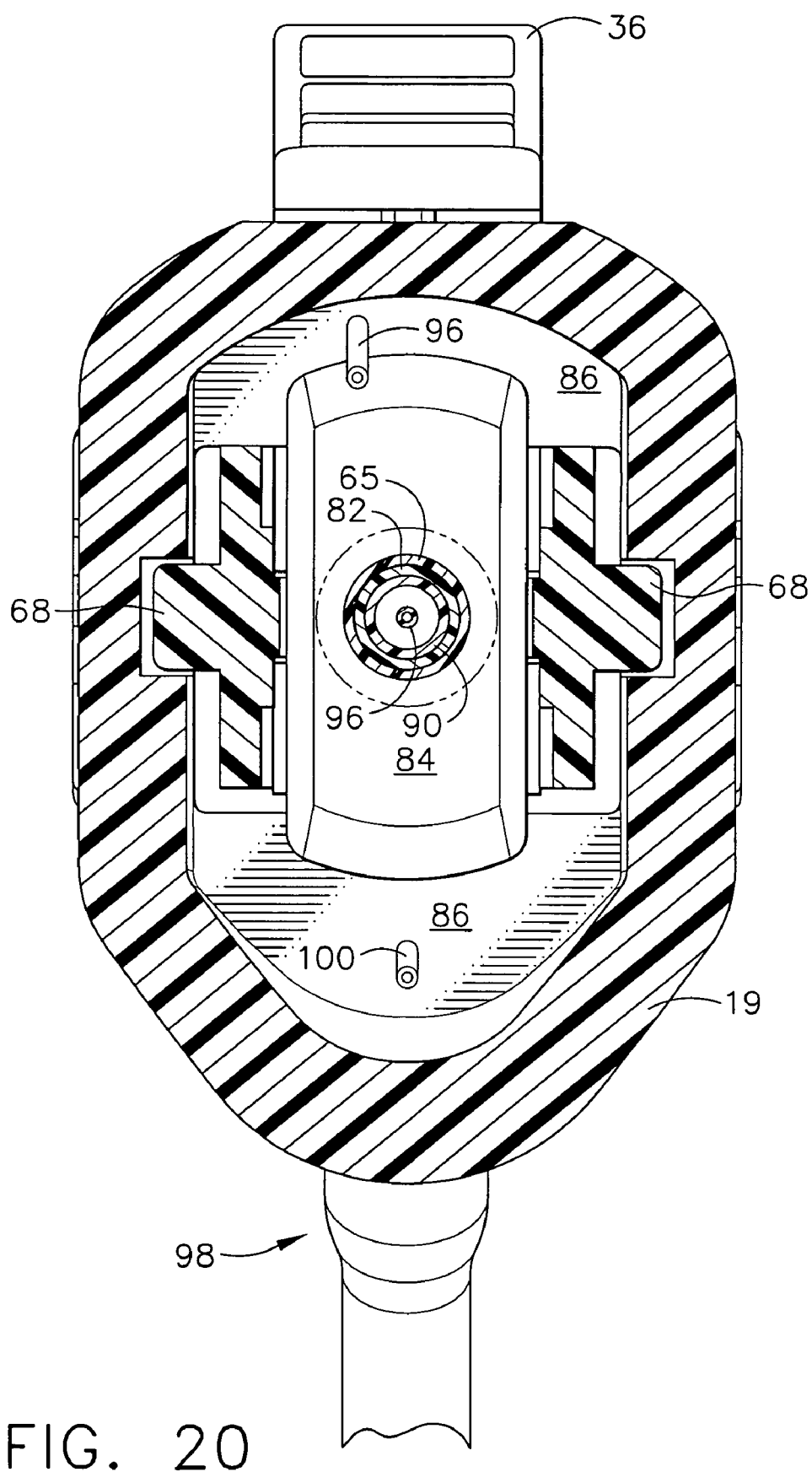
FIG. 20 is a cross-sectional view taken at Plane 20 of the device of FIG. 13.
Figure 21:
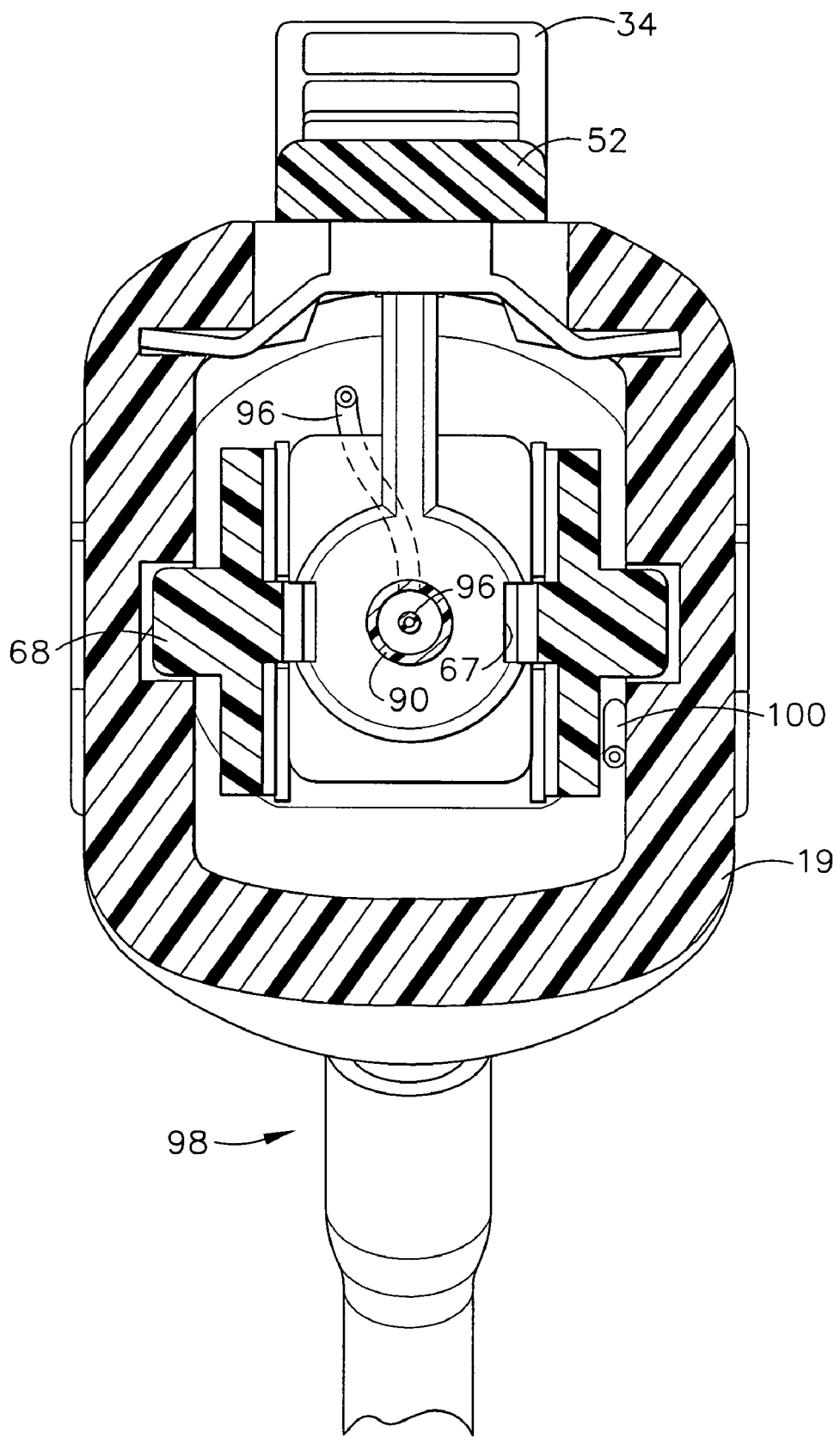
FIG. 21 is a cross-sectional view taken at Plane 21 of the device of FIG. 13.

In response to receiving a pressurized medium, each balloon 30, 32 may inflate. As an alternative to balloons 30, 32, any other inflatable member or expanding member may be used. In addition, while two balloons 30, 32 are shown, it will be appreciated that any number of inflatable members may be used. Suitable materials for making balloons 30, 32 will be apparent to those of ordinary skill in the art. Those of ordinary skill in the art will appreciate that, with an anastomotic ring in place, balloons 30, 32 may be inflated near or adjacent the anastomosis site to provide a seal of the affected lumens. Such a seal may be useful for, inter alia, leak and/or pressure testing of the anastomosis. Inflation of balloons 30, 32 is shown in FIGS. 10 and 19.

While the applier 10 of the present example employs splitter 94 to direct a pressurized medium to each balloon 30, 32, it will be appreciated that a variety of other structures may be used. By way of example only, one or more valves may be used to provide inflation of one balloon 30, 32 at a time, and/or to otherwise regulate the pressure of each balloon individually. Alternatively, each balloon 30, 32 may have its own respective balloon port. Still other suitable alternatives will be apparent to those of ordinary skill in the art.

In addition, handle 19 further comprises an insufflation port 98, which is positioned at the bottom of handle 19 at the proximal end of handle 19. Insufflation port 98 is configured to receive a pressurized medium, such as air, liquid, or the like, from an external source. Insufflation tube 100 is in fluid communication with insufflation port 98. The distal end of insufflation tube 100 is located inside sheath 24, outside outer tube 80, and opens into sheath 24. Accordingly, and as shown in FIG. 19, a pressurized medium such as air may be introduced to the anastomosis site for insufflation or other purposes by communicating such pressurized medium through the insufflation port 98 and insufflation tube 100, whereby the pressurized medium will enter the anastomosis site via the open end of sheath 24. Alternatively, insufflation tube 100 may open at any suitable location, and/or the anastomosis site may be insufflated by any other suitable means, device, or method. In any event, such insufflation may be useful for leak and/or pressure testing the anastomosis while balloons 30, 32 are inflated as described above or under other conditions.

While, in the present example, a pressurized medium is communicated to ports 92, 98 from an external source, it will appreciated that a pressurized medium need not come from an external source. By way of example only, applier 10 may have a pressurized vessel containing a pressurized medium housed within or proximately attached to applier 10. Such a vessel may provide a pressurized fluid medium to either port 92, 98 or both ports 92, 98.

Figure 5:
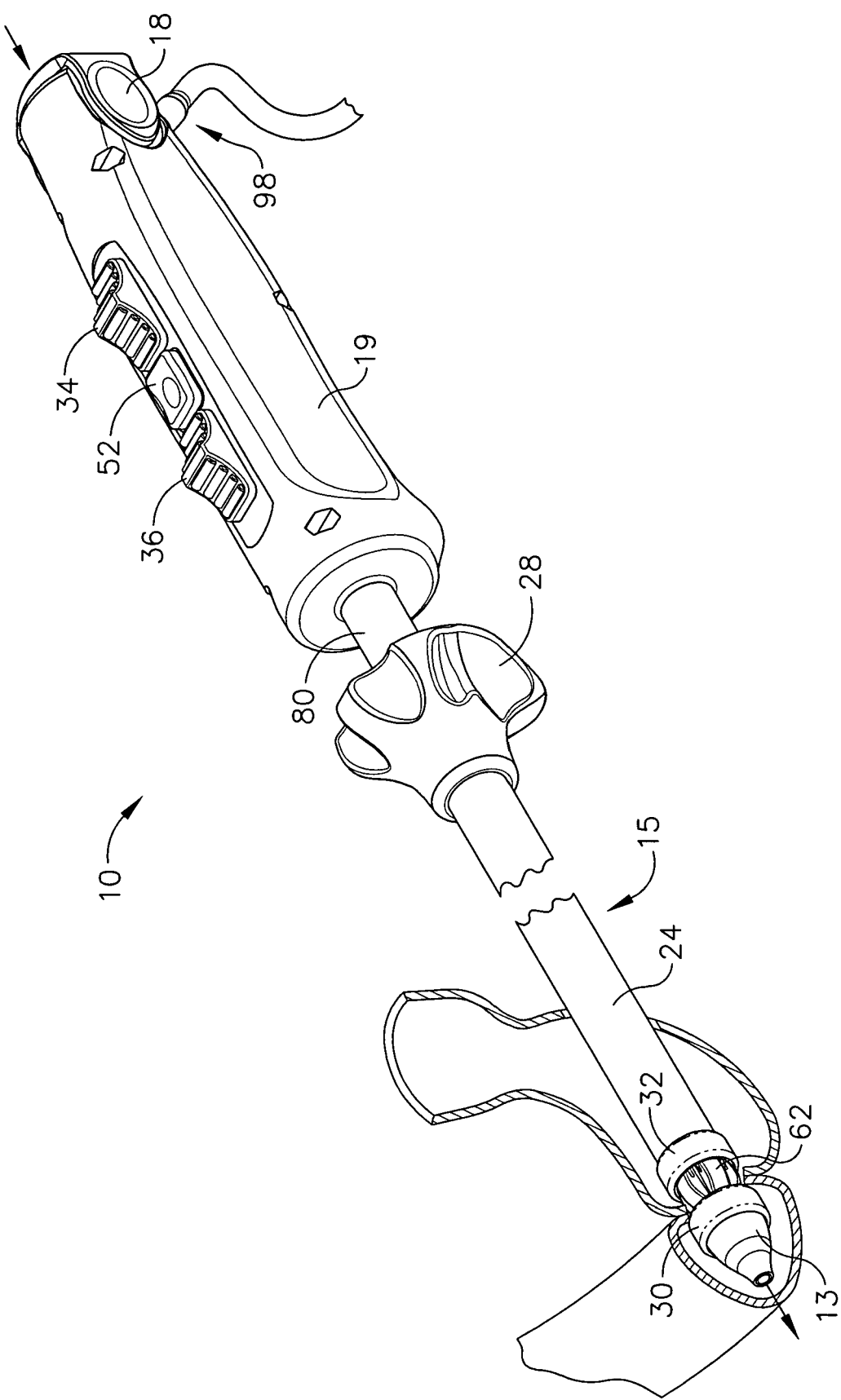
FIG. 5 is a perspective view of the device of FIG. 1, shown with the tip extended.
Figure 9:
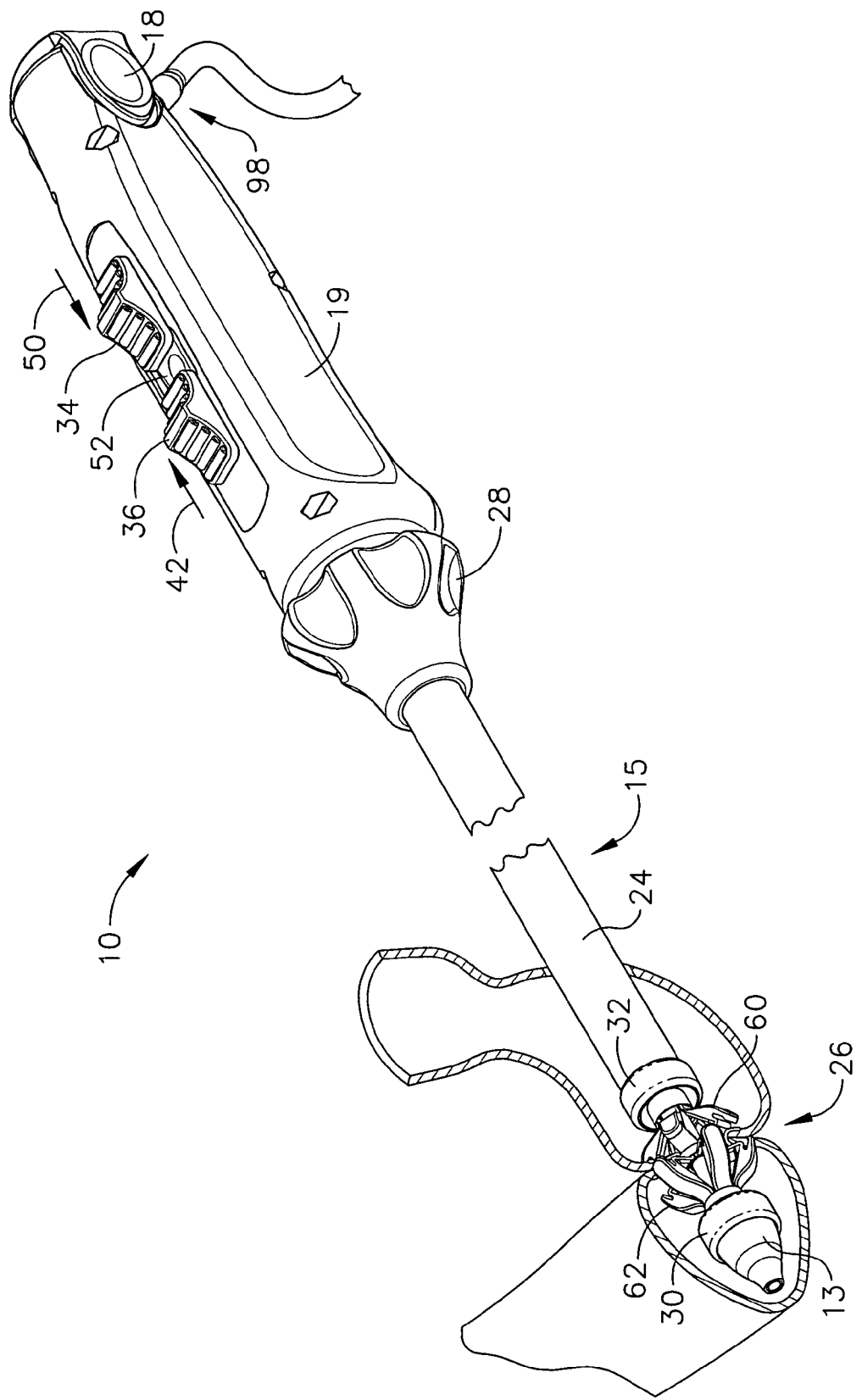
FIG. 9 is a perspective view of the device of FIG. 1, shown with both a distal portion and a proximal portion of the ring deployment mechanism fully actuated.
Figure 15:
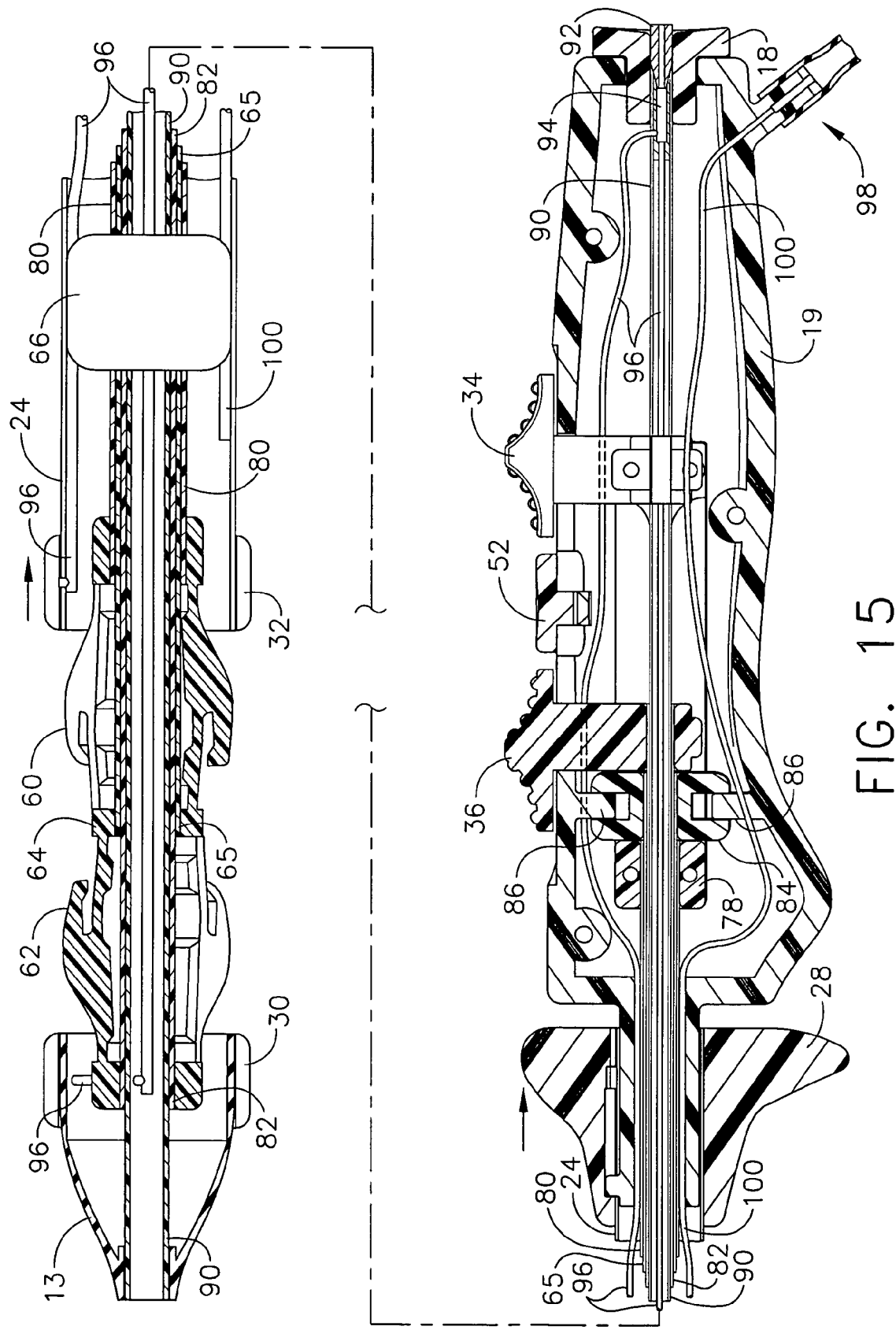
FIG. 15 is a partial cross-sectional view of distal and proximal portions of the device of FIG. 1, shown with the sheath retracted.
Figure 16:
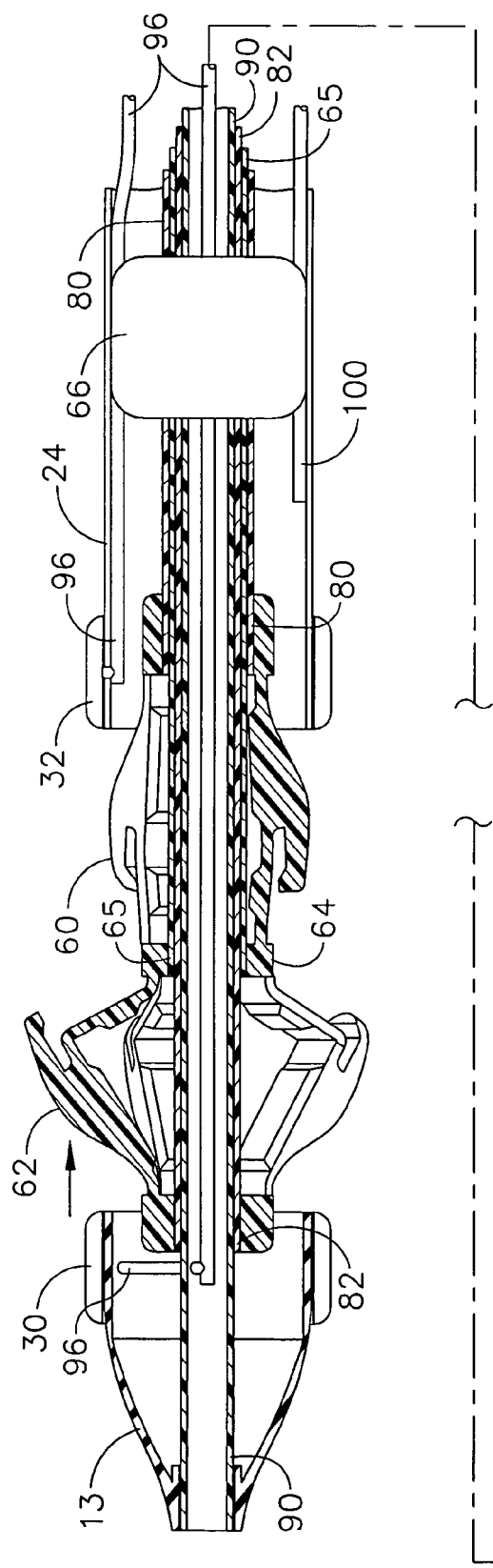
FIG. 16 is a partial cross-sectional view of distal and proximal portions of the device of FIG. 1, shown with a distal portion of the ring deployment mechanism actuated.
Figure 16:
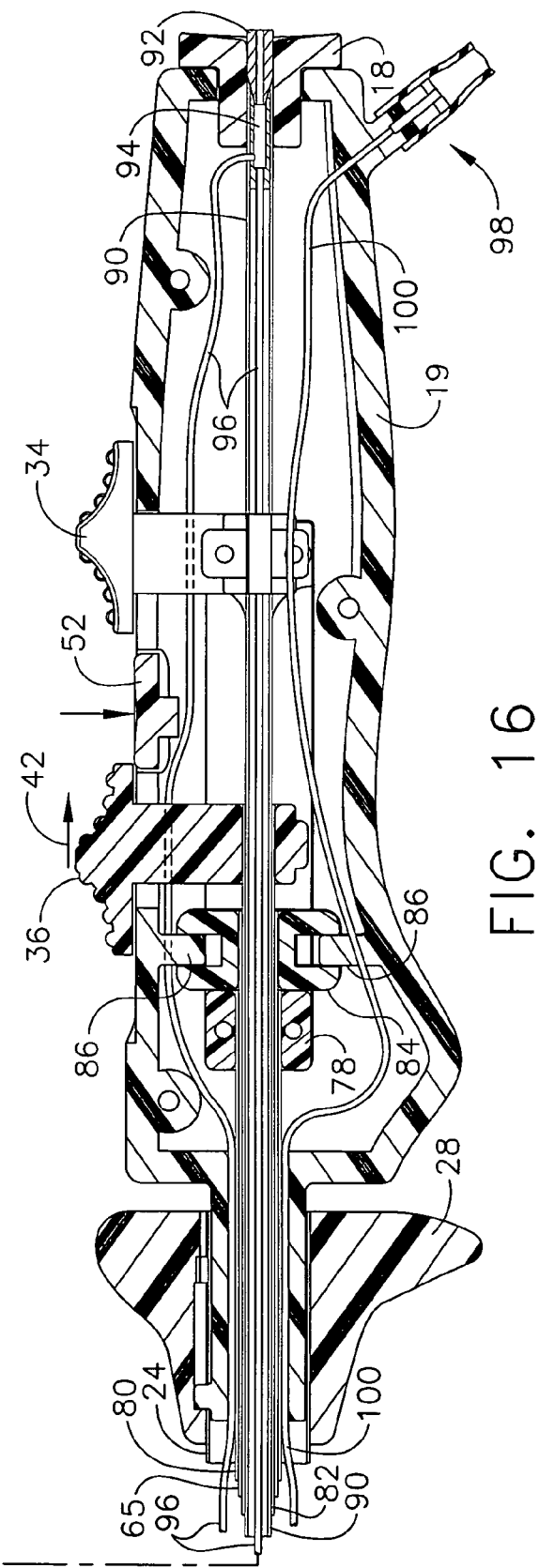
Figure 17:
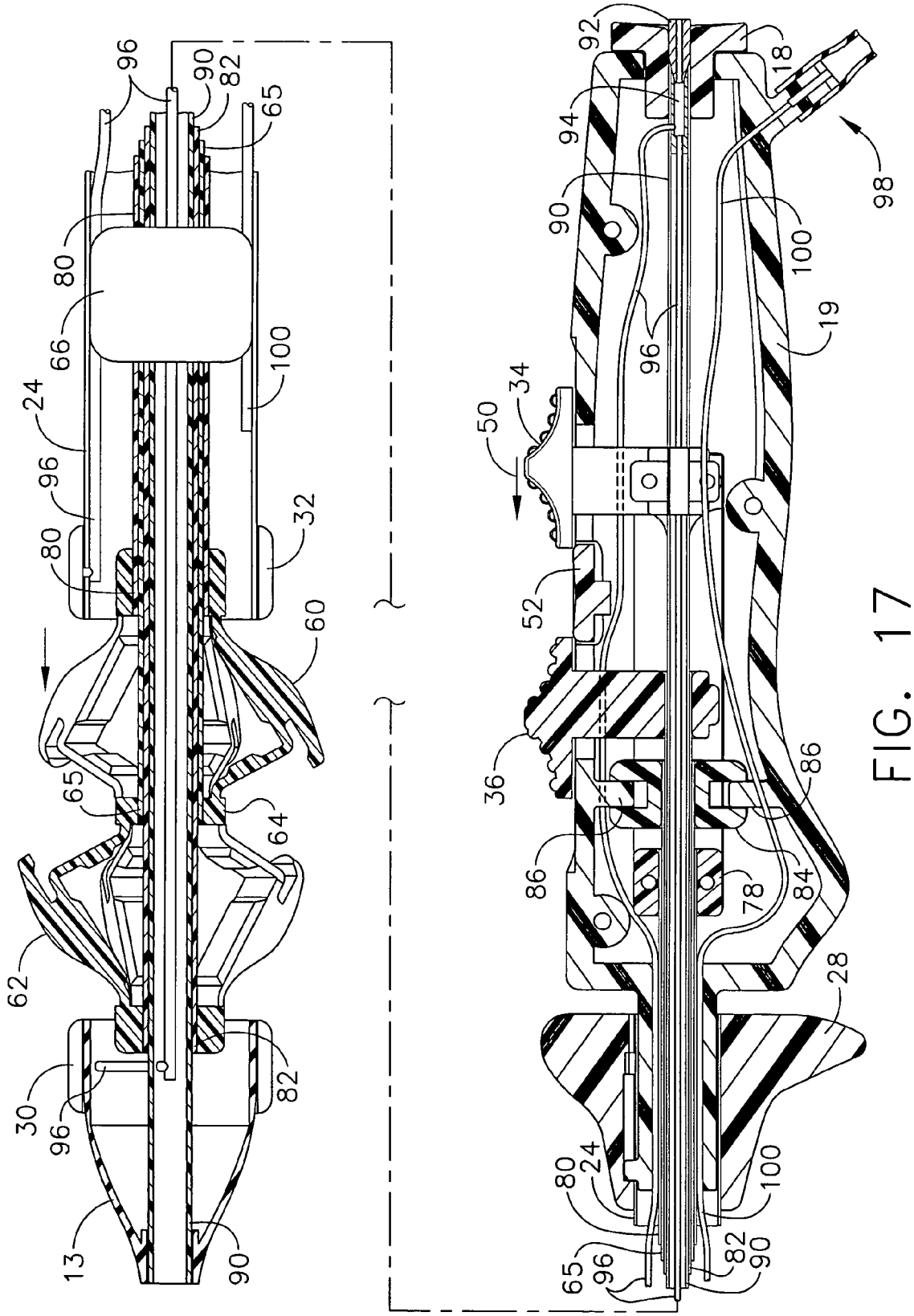
FIG. 17 is a partial cross-sectional view of distal and proximal portions of the device of FIG. 1, shown with both a distal portion and a proximal portion of the ring deployment mechanism partially actuated.
Figure 18:
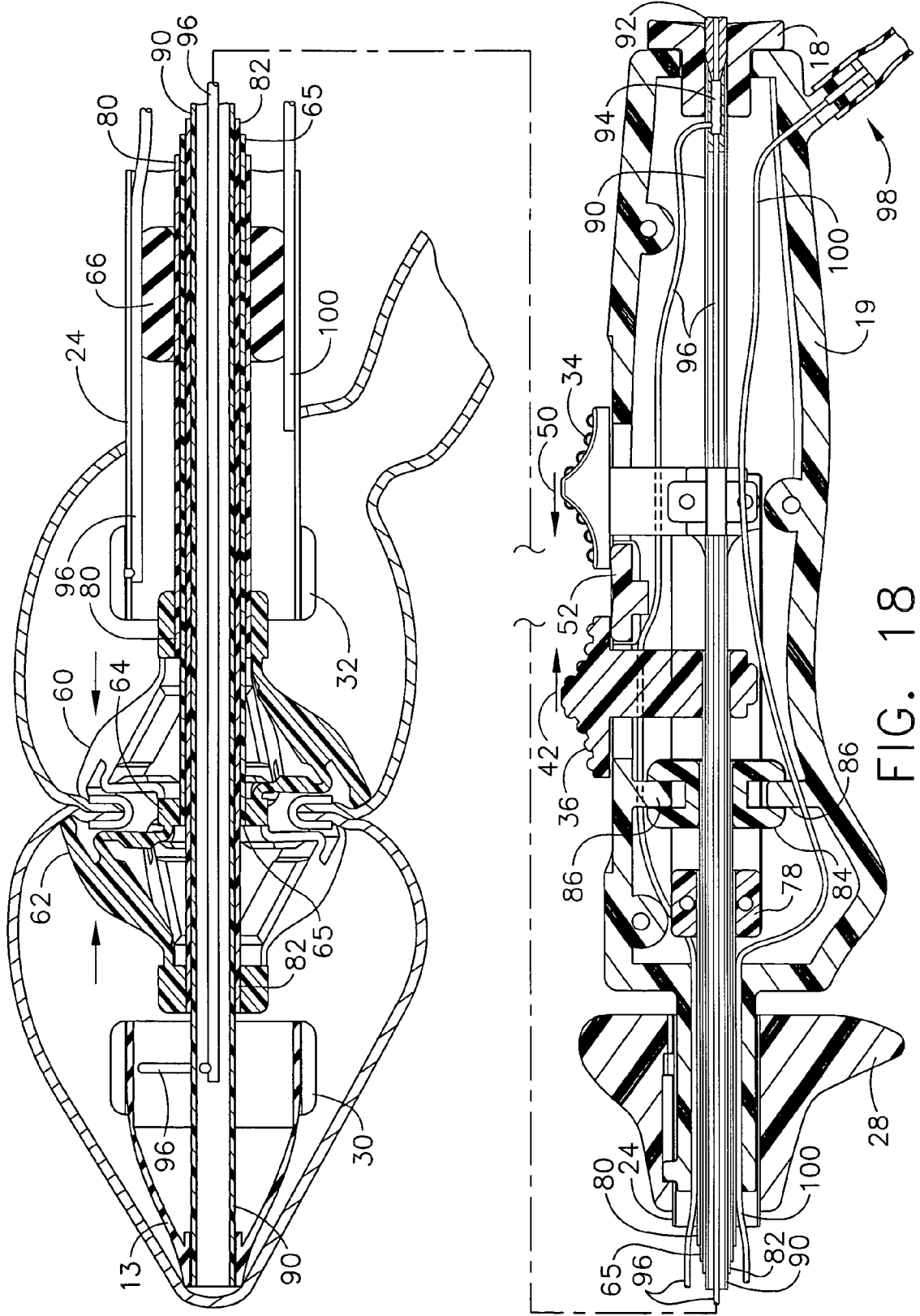
FIG. 18 is a partial cross-sectional view of distal and proximal portions of the device of FIG. 1, shown inserted through an anastomotic opening with both a proximal and a distal portion of a ring deployment mechanism fully actuated.

In use, applier 10 may be inserted adjacent an anastomotic opening in proximate tissue walls. Tip 13 may initially be located in the retracted position, as depicted in FIGS. 1 and 13, during insertion. Once tip 13 has been inserted through the anastomotic opening, tip 13 may be extended using tip actuator 18, as depicted in FIGS. 5 and 14. Sheath actuator 28 may be used to retract sheath 24 to expose ring deployment mechanism 26, as shown in FIGS. 6 and 15. With ring deployment mechanism 26 exposed, and with locking element 52 depressed, second actuator 36 may be actuated, thereby causing actuation of distal fingers 62, as shown in FIGS. 7 and 16. Next, first actuator 34 may be actuated, thereby causing actuation of proximal fingers 60, as shown in FIGS. 8 and 17. First and second actuators 34, 36 may be fully actuated, as shown in FIGS. 9 and 18, to deploy an anastomotic ring. Upon deployment of the anastomotic ring, balloons 30, 32 may be inflated as shown in FIGS. 10 and 19, and the anastomosis area insufflated, to test the anastomosis for leaks or other purposes. As shown, applier 10 may be repositioned, such as by moving applier 10 proximally, before inflation and/or insufflation. Other suitable positions for applier 10 during inflation and/or insufflation will be apparent to those of ordinary skill in the art. Upon completion of testing, balloons 30, 32 may be deflated, and fingers 60, 62 deactuated, and applier 10 may be removed. Still other uses for applier 10 will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument operable to test an anastomosis, wherein the anastomosis is located at an anastomosis site in a patient, the instrument comprising:
   (a) a handle;
   (b) a tip;
   (c) a tip actuator, wherein the tip actuator is configured to move the tip from a retracted position to an extended position;
   (d) a shaft connected to the handle, the shaft comprising:
      (i) an outer surface,
      (ii) a proximal end, wherein the handle is located at the proximal end of the shaft,
      (iii) a distal end, wherein the distal end of the shaft comprises two or more inflatable members adjacent the outer surface, wherein the two or more inflatable members are spaced to permit at least one inflatable member of the two or more inflatable members to be positioned on a first side of the anastomosis and another at least one inflatable member of the two or more inflatable members to be positioned on a second side of the anastomosis, wherein the at least one inflatable member is configured to provide a seal of at least one of the one or more lumens, wherein the seal is adjacent the anastomosis, wherein the seal is provided upon inflation of the at least one inflatable member,
      (iv) one or more conduits configured to communicate a pressurized medium to at least one of the two or more inflatable members, and
      (v) a tubular sheath, wherein the tubular sheath is moveable from a first position to a second position;
   (e) a ring deployment mechanism located at the distal end of the shaft adjacent the two or more inflatable members, wherein the ring deployment mechanism is operable to deploy an anastomotic ring at the anastomosis site, wherein the ring deployment mechanism defines a longitudinal axis, wherein the ring deployment mechanism comprises:
      (i) a proximal ring situated about said longitudinal axis,
      (ii) a first plurality of fingers, wherein each finger of the first plurality of fingers comprises a proximal segment and a distal segment, wherein the proximal segment of each finger of the first plurality of fingers is hingedly connected to the corresponding distal segment of the same finger of the first plurality of fingers at a corresponding finger joint, wherein the proximal segment of each finger of the first plurality of fingers is further hingedly connected to said proximal ring, wherein the first plurality of fingers are configured to engage the anastomotic ring at regions adjacent to the finger joints of the first plurality of fingers,
      (iii) a distal ring situated about said longitudinal axis,
      (iv) a second plurality of fingers, wherein each finger of the second plurality of fingers comprises a proximal segment and a distal segment, wherein the proximal segment of each finger of the second plurality of fingers is hingedly connected to the corresponding distal segment of the same finger of the second plurality of fingers at a corresponding finger joint, wherein the distal segment of each finger of the second plurality of fingers is further hingedly connected to said distal ring, wherein the second plurality of fingers are configured to engage the anastomotic ring at regions adjacent to the finger joints of the second plurality of fingers, and
      (v) a middle ring positioned in between said proximal ring and said distal ring, wherein the distal segment of each finger of the first plurality of fingers is further hingedly connected to the middle ring, wherein the proximal segment of each finger of the second plurality of fingers is further hingedly connected to the middle ring, wherein the middle ring longitudinally separates the distal segments of the first plurality of fingers from the proximal segments of the second plurality of fingers;
   (f) one or more actuators operable to actuate the ring deployment mechanism, wherein the one or more actuators is configured to move along the handle or the shaft; and
   (g) a tip tube positioned within the shaft, wherein the tip tube has a proximal end and a distal end, wherein the proximal end of the tip tube is coupled with the tip actuator, wherein the distal end of the tip tube is coupled with the tip, wherein the tip actuator is operable to move the tip from a retracted position relative to the tubular sheath to an extended position relative to the tubular sheath via the tip tube;
   wherein the tip is configured to cover a distal portion of the ring deployment mechanism when the tip is in the retracted position;
   wherein the tip is configured to uncover the distal portion of the ring deployment mechanism when the tip is in the extended position;
   wherein the tubular sheath is configured to cover a proximal portion of the ring deployment mechanism when the tubular sheath is in the first position;
   wherein the tubular sheath is configured to uncover the proximal portion of the ring deployment mechanism when the tubular sheath is in the second position.

2. The instrument of claim 1, further comprising an insufflation member, wherein the insufflation member is configured to communicate a pressurized medium to the anastomosis site.

3. The instrument of claim 2, wherein the insufflation member comprises an insufflation tube, wherein the insufflation tube is positioned along the shaft.

4. The instrument of claim 2, wherein the handle comprises an insufflation port, wherein the insufflation port is in fluid communication with the insufflation member, wherein the insufflation port is configured to receive a pressurized medium.

5. The instrument of claim 1, wherein the handle comprises an inflation port, wherein the inflation port is in fluid communication with at least one of the one or more conduits, wherein the inflation port is configured to receive a pressurized medium.

6. The instrument of claim 1, wherein the two or more inflatable members comprise a pair of circumferential balloons.

7. The instrument of claim 1, wherein the ring deployment mechanism is positioned between a pair of inflatable members of the two or more inflatable members.

8. The instrument of claim 1, wherein the handle comprises the one or more actuators.

9. The instrument of claim 1, wherein the shaft further comprises one or more longitudinal members configured to transmit one or more actuating forces to the ring deployment mechanism, wherein the ring deployment mechanism is configured to actuate in response to the one or more actuating forces.

10. A surgical instrument operable to test an anastomosis, wherein the anastomosis is located at an anastomosis site in a patient, wherein the anastomosis site comprises two or more lumens and an opening, the instrument comprising:
(a) an elongate shaft;
(b) a ring deployment mechanism in communication with the shaft, wherein the ring deployment mechanism is operable to deploy an anastomotic ring device at the anastomosis site, wherein the anastomotic ring device is moveable from a first position to a second position, wherein the first position is a compressed, cylindrically-shaped position and the second position is an actuated, hollow rivet-shaped position, wherein the ring deployment mechanism defines a longitudinal axis, wherein the ring deployment mechanism comprises:
(i) a proximal ring situated about said longitudinal axis,
(ii) a first plurality of fingers, wherein each finger of the first plurality of fingers comprises a proximal segment and a distal segment, wherein the proximal segment of each finger of the first plurality of fingers is hingedly connected to the corresponding distal segment of the same finger of the first plurality of fingers at a corresponding finger joint, wherein the proximal segment of each finger of the first plurality of fingers is further hingedly connected to said proximal ring, wherein the first plurality of fingers are configured to engage the anastomotic ring device at regions adjacent to the finger joints of the first plurality of fingers,
(iii) a distal ring situated about said longitudinal axis,
(iv) a second plurality of fingers, wherein each finger of the second plurality of fingers comprises a proximal segment and a distal segment, wherein the proximal segment of each finger of the second plurality of fingers is hingedly connected to the corresponding distal segment of the same finger of the second plurality of fingers at a corresponding finger joint, wherein the distal segment of each finger of the second plurality of fingers is further hingedly connected to said distal ring, wherein the second plurality of fingers are configured to engage the anastomotic ring device at regions adjacent to the finger joints of the second plurality of fingers, and
(v) a middle ring positioned in between said proximal ring and said distal ring, wherein the distal segment of each finger of the first plurality of fingers is further hingedly connected to the middle ring, wherein the proximal segment of each finger of the second plurality of fingers is further hingedly connected to the middle ring, wherein the middle ring longitudinally separates the distal segments of the first plurality of fingers from the proximal segments of the second plurality of fingers;
(c) at least one inflatable member in communication with the shaft, wherein the at least one inflatable member is configured to provide a seal of at least one of the one or more lumens, wherein the seal is adjacent the anastomosis, wherein the seal is provided upon inflation of the at least one inflatable member, wherein the at least one inflatable member is configured to inflate to a diameter substantially larger than the opening in the anastomosis site;
(d) an insufflation member having an open distal end that is positionable within one of the lumens of the anastomosis site, wherein the insufflation member is configured to communicate a pressurized medium to the anastomosis site, wherein the insufflation member is fluidly independent of the at least one inflatable member; and
(e) one or more conduits configured to communicate a pressurized medium, wherein the one or more conduits are in fluid communication with at least one of:
(i) the at least one inflatable member, or
(ii) the insufflation member.

11. The surgical instrument of claim 10, further comprising a handle connected to the shaft, wherein the one or more conduits are located along the shaft, wherein the handle comprises one or more ports, wherein each port of the one or more ports is in communication with at least one of the one or more conduits, wherein the one or more ports are configured to receive a pressurized medium.

* * * * *